(12) United States Patent
Yonemura et al.

(10) Patent No.: US 11,882,835 B2
(45) Date of Patent: Jan. 30, 2024

(54) BENZIMIDAZOLE COMPOUND HAVING AN OPTIONALLY HALOGENATED ALKYLENEDIOXY GROUP OR SALT THEREOF, AGRICULTURAL AND HORTICULTURAL INSECTICIDE COMPRISING THE COMPOUND OR THE SALT, AND METHOD FOR USING THE INSECTICIDE

(71) Applicant: NIHON NOHYAKU CO., LTD., Tokyo (JP)

(72) Inventors: Ikki Yonemura, Osaka (JP); Shunpei Fujie, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 599 days.

(21) Appl. No.: 17/258,939

(22) PCT Filed: Jul. 9, 2019

(86) PCT No.: PCT/JP2019/027062
§ 371 (c)(1),
(2) Date: Jan. 8, 2021

(87) PCT Pub. No.: WO2020/013147
PCT Pub. Date: Jan. 16, 2020

(65) Prior Publication Data
US 2021/0329920 A1 Oct. 28, 2021

(30) Foreign Application Priority Data

Jul. 10, 2018 (JP) ................................ 2018-130652

(51) Int. Cl.
*A01N 43/90* (2006.01)
*A61P 33/14* (2006.01)
*A61K 9/00* (2006.01)
*C07D 491/056* (2006.01)

(52) U.S. Cl.
CPC ............ *A01N 43/90* (2013.01); *A61K 9/0017* (2013.01); *A61K 9/0053* (2013.01); *A61P 33/14* (2018.01); *C07D 491/056* (2013.01)

(58) Field of Classification Search
CPC ....... A01N 43/90; A61P 33/14; A61K 9/0017; A61K 9/0053; C07D 491/056
USPC ........................................................ 514/338
See application file for complete search history.

(56) References Cited

U.S. PATENT DOCUMENTS

| 5,731,300 | A | 3/1998 | Assmann et al. |
| 5,932,605 | A | 8/1999 | Assmann et al. |
| 6,103,745 | A | 8/2000 | Assmann et al. |
| 2016/0002260 | A1 | 1/2016 | Tanabe et al. |
| 2017/0260214 | A1 | 9/2017 | Stoller et al. |
| 2017/0318809 | A1 | 11/2017 | Edmunds et al. |
| 2017/0342065 | A1 | 11/2017 | Hueter et al. |
| 2018/0002347 | A1 | 1/2018 | Yonemura et al. |
| 2018/0116222 | A1 | 5/2018 | Fischer et al. |
| 2018/0271099 | A1 | 9/2018 | Fischer et al. |
| 2018/0305353 | A1 | 10/2018 | Fischer et al. |
| 2018/0346462 | A1 | 12/2018 | Jung et al. |
| 2019/0308971 | A1 | 10/2019 | Hueter et al. |
| 2020/0029567 | A1 | 1/2020 | Fischer et al. |
| 2020/0045975 | A1 | 2/2020 | Sano et al. |
| 2020/0214292 | A1 | 7/2020 | Yonemura et al. |

FOREIGN PATENT DOCUMENTS

| JP | 9-512801 | 12/1997 |
| WO | 2014/132971 | 9/2014 |
| WO | 2016/026848 | 2/2016 |
| WO | 2016/071214 | 5/2016 |

(Continued)

OTHER PUBLICATIONS

International Search Report dated Sep. 24, 2014 in International (PCT) Application No. PCT/JP2019/027062.
International Preliminary Report on Patentability and Written Opinion of the International Searching Authority dated Jan. 12, 2021 in International (PCT) Application No. PCT/JP2019/027062.

*Primary Examiner* — Kristin A Vajda
(74) *Attorney, Agent, or Firm* — Wenderoth, Lind & Ponack, L.L.P.

(57) ABSTRACT

Provided are a benzimidazole compound represented by the general formula (1)

[Chem. 1]

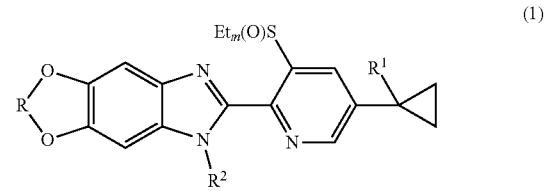

(1)

{wherein $R^1$ represents a hydrogen atom or a cyano group, $R^2$ represents a ($C_1$-$C_6$) alkyl group, a ($C_1$-$C_6$) alkoxy ($C_1$-$C_6$) alkyl group, or a halo ($C_1$-$C_6$) alkyl group, R represents a ($C_1$-$C_3$) alkylene group or a halo ($C_1$-$C_3$) alkylene group, and m represents 0, 1, or 2}, or a salt thereof, an agricultural and horticultural insecticide comprising the compound or the salt as an active ingredient; an animal ectoparasite or endoparasite control agent comprising the compound or the salt as an active ingredient; and a method for using the insecticide or the agent.

15 Claims, No Drawings

(56) References Cited

FOREIGN PATENT DOCUMENTS

| | | |
|---|---|---|
| WO | 2016/096584 | 6/2016 |
| WO | 2016/104746 | 6/2016 |
| WO | 2016/121997 | 8/2016 |
| WO | 2016/162318 | 10/2016 |
| WO | 2017/025419 | 2/2017 |
| WO | 2017/072039 | 5/2017 |
| WO | 2017/089190 | 6/2017 |
| WO | 2018/070502 | 4/2018 |
| WO | 2019/059244 | 3/2019 |

BENZIMIDAZOLE COMPOUND HAVING AN OPTIONALLY HALOGENATED ALKYLENEDIOXY GROUP OR SALT THEREOF, AGRICULTURAL AND HORTICULTURAL INSECTICIDE COMPRISING THE COMPOUND OR THE SALT, AND METHOD FOR USING THE INSECTICIDE

TECHNICAL FIELD

The present invention relates to a benzimidazole compound having an optionally halogenated alkylenedioxy group (hereinafter may be referred to simply as an alkylenedioxy group) or a salt thereof, an agricultural and horticultural insecticide comprising the compound or the salt as an active ingredient, and a method for using the insecticide.

BACKGROUND ART

Various compounds have been examined for their potential as agricultural and horticultural insecticides, and among them, certain kinds of cyclopropylpyridyl compounds have been reported to be useful as insecticides (for example, see Patent Literature 1 to 5). The literature, however, does not disclose any compound in which an alkylenedioxy group is bound to a benzimidazole ring.

CITATION LIST

Patent Literature

Patent Literature 1: WO 2016/026848
Patent Literature 2: WO 2016/071214
Patent Literature 3: WO 2016/096584
Patent Literature 4: WO 2016/101746
Patent Literature 5: WO 2016/121997

SUMMARY OF INVENTION

Technical Problem

In crop production in the fields of agriculture, horticulture and the like, the damage caused by insect pests etc. is still immense. Addressing this issue requires agricultural and horticultural insecticides which are effective for controlling emerged drug-resistant insect pests with limited impact on bioindicators, labor-saving of operation, securing of operator's safety, etc.; and which are also characterized by having less impact on nontarget organisms such as natural predators and useful insects; being active as systemic insecticides; having ±ow toxicity for mammals including humans; having less impact on bioindicators such as fish and birds; having a similar effect across different species; having environmental degradability; and the like. Therefore, the development of novel agricultural and horticultural insecticides having such excellent properties is desired. In addition, the development of novel agents capable of controlling animal ectoparasites and endoparasites is also desired.

Solution to Problem

The present inventors conducted extensive research to solve the above-mentioned problems. As a result, the present inventors found that the alkylenedioxy group-containing benzimidazole compound represented by the general formula (1) below or a salt thereof is very useful as a solution to the above-mentioned problems in that the compound or the salt is not only highly effective for the control of agricultural and horticultural pests, but also has little impact on nontarget organisms such as natural predators and useful insects and environmental degradability. This compound was also found to be capable of controlling animal ectoparasites and endoparasites. Based on these findings, the present inventors further conducted a great deal of examination and completed the present invention.

That is, the present invention includes the following.

[1] A benzimidazole compound represented by:

[Chem. 1]

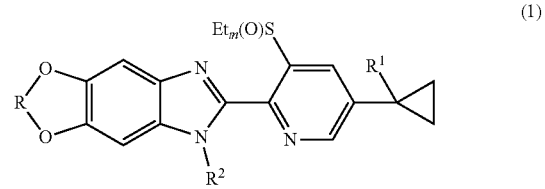

{wherein
R$^1$ represents
(a1) a hydrogen atom; or
(a2) a cyano group,
R$^2$ represents
(b1) a ($C_1$-$C_5$) alkyl group;
(b2) a ($C_1$-$C_6$) alkoxy ($C_1$-$C_6$) alkyl group; or
(b3) a halo ($C_1$—C) alkyl group,
R represents
(c1) a ($C_1$-$C_3$) alkylene group; or
(c2) a halo ($C_1$-$C_3$) alkylene group, and
m represents 0, 1, or 2}, or
a salt thereof.

[2] The benzimidazole compound or the salt according to the above [1], wherein
R$^1$ represents
(a1) a hydrogen atom; or
(a2) a cyano group,
R$^2$ represents
(b1) a ($C_1$-$C_6$) alkyl group;
(b2) a ($C_1$-$C_6$) alkoxy ($C_1$-$C_6$) alkyl group; or
(b3) a halo ($C_1$-$C_6$) alkyl group,
R represents
(c2) a halo ($C_1$-$C_3$) alkylene group, and
m represents 0, 1, or 2.

[3] The benzimidazole compound or the salt according to the above [1], wherein
R$^1$ represents (a1) a hydrogen atom,
R$^2$ represents (b1) a ($C_1$-$C_6$) alkyl group,
R represents (c2) a halo ($C_1$-$C_3$) alkylene group, and
m represents 2.

[4] An agricultural and horticultural insecticide comprising the benzimidazol e compound or the salt according to any one of the above [1] to [3] as an active ingredient.

[5] A method for using an agricultural and horticultural insecticide, the method comprising treating plants or soil with an effective amount of the benzimidazole compound or the salt according to any one of the above [1] to [3].

[6] An animal ectoparasite or endoparasite control agent comprising an effective amount of the benzimidazole compound or the salt according to any one of the above [I] to [3] as an active ingredient.

[7] A method for using an animal ectoparasite or endoparasite control agent, the method comprising transdermally applying or orally administering an effective amount of the benzimidazole compound or the salt according to any one of the above [1] to
[3] to an animal.

Advantageous Effects of Invention

The alkylenedioxy group-containing benzimidazole compound of the present invention or a salt thereof is not only highly effective as an agricultural and horticultural insecticide but also effective for the disinfection of pests which live in the interior of or on the exterior of pet animals such as dogs and cats and domestic animals such as cattle and sheep.

DESCRIPTION OF EMBODIMENTS

In the definition of the benzimidazole compound represented by the general formula (1) of the present invention or a salt thereof, "halo" refers to a "halogen atom" and represents a fluorine atom, a chlorine atom, a bromine atom or an iodine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-buty group, a tert-butyl group, a n-pentyl group, an isopentyl group, a tert-pentyl group, a neopentyl group, a 2,3-dimethylpropyl group, an i-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_1-C_3)$ alkylene group" refers to a straight-chain or branched-chain alkylene group of 1 to 3 carbon atoms, for example, a methylene group, an ethylene group, a propylene group, or the like.

The above "$(C_1-C_6)$ alkyl group" and "$(C_1-C_3)$ alkylene group" may be substituted with one or more halogen atoms at a substitutable position (s) in place of a hydrogen atom(s), and in the case where any of these groups is substituted with two or more halogen atoms, the two or more halogen atoms may be the same or different.

The above-mentioned "groups substituted with one or more halogen atoms" are expressed as a "halo $(C_1-C_6)$ alkyl group" and a "halo $(C_1-C_3)$ alkylene group".

The expression "$(C_1-C_6)$" refers to the range of the number of carbon atoms in each group. The same definition holds true for groups in which two or more groups are coupled together, and for example, the "$(C_1-C_6)$ alkoxy $(C_1-C_6)$ alkyl group" means that a straight-chain or branched-chain alkoxy group of 1 to 6 carbon atoms is bound to a straight-chain or branched-chain alkyl group of 1 to 6 carbon atoms. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, or the like.

Examples of the salt of the benzimidazole compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The benzimidazole compound represented by the general formula (1) of the present invention and a salt thereof can have one or more chiral centers in the structural formula and can exist as two or more kinds of optical isomers or diastereomers. All the isomers and mixtures of the isomers at any ratio are also included in the present invention.

In a preferable embodiment of the benzimidazole compound represented by the general formula (1) of the present invention or a salt thereof,
$R^1$ is
(a1) a hydrogen atom; or
(a2) a cyano group,
$R^2$ is
(b1) a $(C_1-C_6)$ alkyl group;
(b2) a $(C_1-C_6)$ alkoxy $(C_1-C_6)$ alkyl group; or
(b3) a halo $(C_1-C_6)$ alkyl group,
R is
(c2) a halo $(C_1-C_3)$ alkylene group, and
n is 0, 1, or 2.
More preferably,
$R^1$ is (a1) a hydrogen atom,
$R^2$ is (b1) a $(C_1-C_6)$ alkyl group,
R is (c2) a halo $(C_1-C_3)$ alkylene group, and
m is 2.

The benzimidazole compound of the present invention or a salt thereof (hereinafter may be abbreviated simply as the benzimidazole compound) can be produced according to, for example, the production methods described below, which are non-limiting examples. The starting compounds used in the production methods of the present invention can be produced by known methods or methods known per se.

Production Method 1

[Chem. 2]

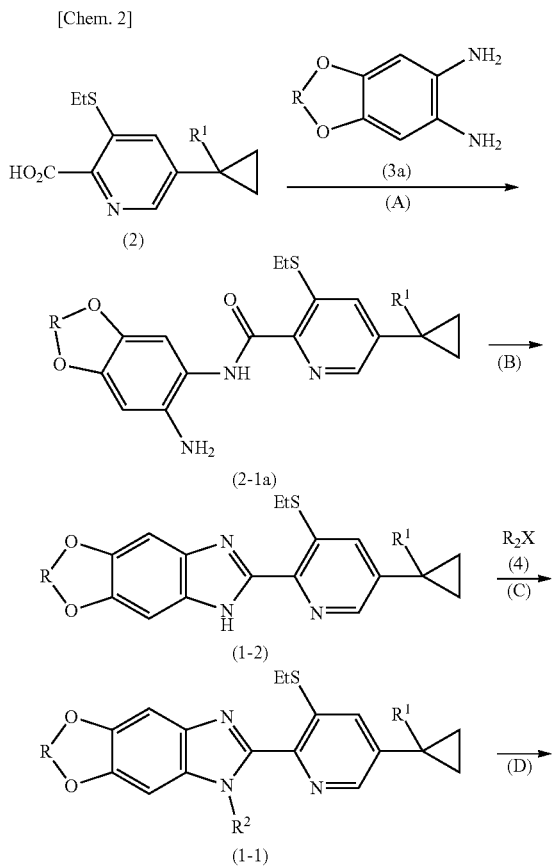

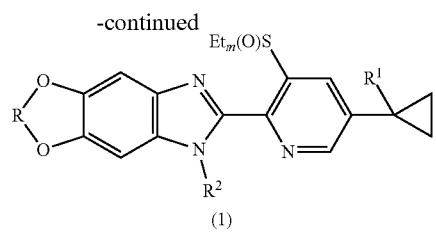

(1)

(In the formula, $R^1$, $R^2$, R, and m are as defined above, and X represents a leaving group.)

Production Method at Step (A)

The amide compound represented by the general formula (2-1a) can be produced by reacting the carboxylic acid represented by the general formula (2) with the diamino compound represented by the general formula (3a) in the presence of a condensing agent, a base, and an inert solvent. The carboxylic acid used in this reaction can be produced by the method described in WO 2016/121997 or WO 2018/07565. The diamino compound used in this reaction can be produced by the method described in the "Production Method of Intermediate" below. The desired compound (2-1a) is optionally isolated by the usual method before use for the production at step (B) described below.

Examples of the condensing agent used in this reaction include diethyl phosphorocyanidate (DEPC), carbonyldiimidazole (CDI), 1,3-dicyclohexylcarbodiimide (DCC), chlorocarbonic esters and 2-chloro-1-methylpyridinium iodide. The amount of the condensing agent used is usually selected as appropriate from the range of a 1- to 1.5-fold molar amount relative to the compound represented by the general formula (2).

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture.

Since this reaction is an equimolar reaction of the reactants, they are basically used in equimolar amounts, but either of them may be used in an excess amount. The reaction temperature may be in the range or room temperature to the boiling point of the inert solvent used. The reaction time varies with the reaction scale and the reaction temperature, but is basically in the range of a few minutes to 48 hours.

After the reaction is completed, the compound or interest is isolated from the post-reaction mixture by the usual method. As needed, recrystallization, column chromatography, etc. can be employed for the purification of the compound of interest. The compound (2-1a) may be subjected to the next step without isolation rom the reaction mixture.

Production Method at Step (B)

The benzimidazole compound represented by the general formula (1-2 can be produced by reacting the amide compound represented by the general formula (2-1a), which was produced by the Production method at step (A), in the presence of an acid and an inert solvent.

Examples of the acid used in this reaction include inorganic acids such as hydrochloric acid, sulfuric acid, nitric acid, and phosphoric acid; organic carboxylic acids such as formic acid, acetic acid, propionic acid, trifluoroacetic acid, and benzoic acid; and sulfonic acids such as methanesulfonic acid, trifluoromethanesulfonic acid, toluenesulfonic acid, and p-toluenesulfonic acid. The amount of the acid used is usually selected as appropriate from the range of a 0.01- to 10-fold molar amount relative to the amide compound represented by the general formula (2-1a).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide, N-methyl pyrrolidone, and 1,3-dimethyl-2-imidazolidinone. One of these inert solvents may be used alone, and also two or more of them may be used as a mixture.

After the reaction is completed, the compound of interest is isolated from the post-reaction mixture by the usual method. As needed, recrystallization, column chromatography, etc. can be employed for the purification of the compound of interest.

Production Method at Step (C)

The benzimidazole compound represented by the general formula (1-1) can be produced by reacting the benzimidazole compound represented by the general formula (1-2) with the compound represented by the general formula (4) in the presence of a base and an inert solvent.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; acetates such as sodium acetate and potassium acetate; alkali metal hydrides such as lithium hydride, sodium hydride, and potassium hydride; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (1-2).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene: straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture.

Since this reaction is an equimolar reaction of the reactants, both the reactants, namely, the compound represented by the general formula (1-2) and the compound represented by the general formula (4) are used basically in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method at Step (D)

The benzimidazole compound represented by the general formula (1) can be produced by reacting the benzimidazole compound represented by the general formula (1-1) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is usually selected as appropriate from the range of a 0.8- to 5-fold molar amount relative to the benzimidazole compound represented by the general formula (1-1).

The inert solvent used in this reaction may be any solvent that does not markedly inhibit the reaction, and examples include straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method 2

[Chem. 3]

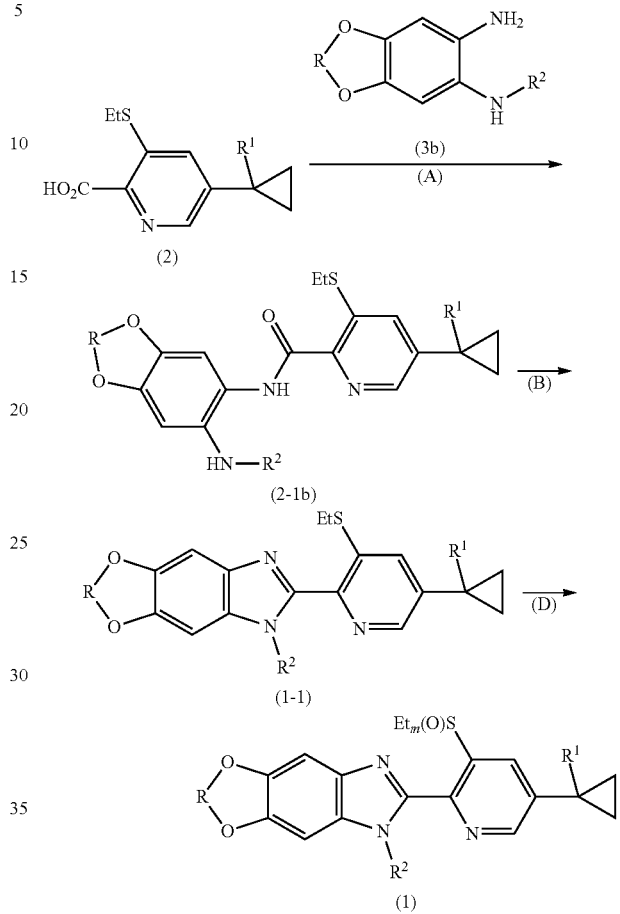

(In the formula $R^1$, $R^2$, R, and m are as defined above.

Steps (A), (B), and (D) can be performed as described in the corresponding steps of the above Production Method 1. The compound represented by the general formula (3b) can be easily produced from the compound of the general formula (3a) by a known method or a method known per se.

The compound represented by the general formula (3a), which is an intermediate for the production of the compound of the present invention, can be produced by the following scheme.

Production Method of Intermediate (3a)

[Chem. 4]

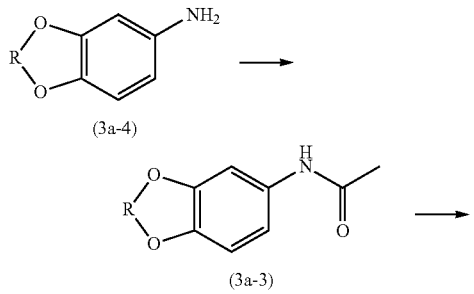

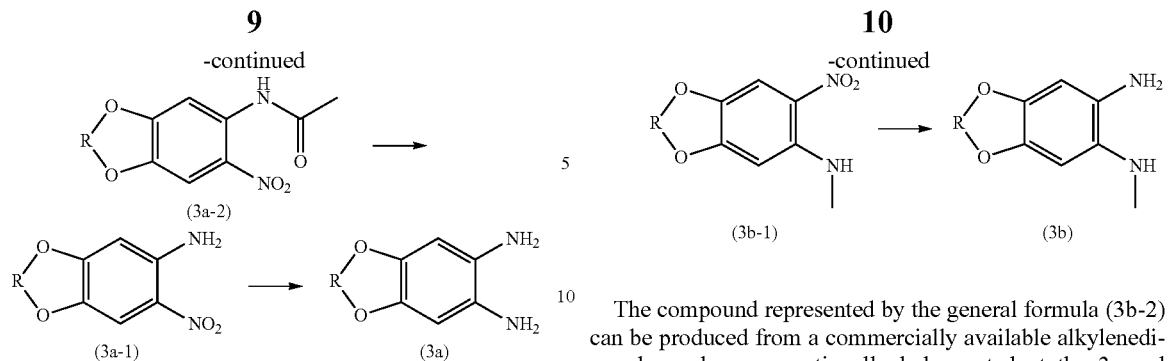

The compound represented by the general formula (3a-3) can be produced from a commercially available alkylenedioxy aniline optionally halogenated at the 3- and 4-positions (3a-4) according to the method described in Greene's PROTECTIVE GROUPS in ORGANIC Synthesis 4th Edition, page 773 (John Wiley & Sons, Inc.). After the reaction is completed, the compound of interest is isolated from the post-reaction mixture by the usual method. As needed, recrystallization, column chromatography, etc. can be employed for the purification of the compound of interest.

The compound represented by the general formula (3a-2) can be produced from the compound represented by the general formula (3a-3) according to the method described in ORGANIC FUNCTION GROUP PREPARATIONS I 2nd Edition, Chapter 16, Sandler Karo (ACADEMIC PRESS, INC. (LONDON) LTD.). After the reaction is completed, the compound of interest is isolated from the post-reaction mixture by the usual method. As needed, recrystallization, column chromatography, etc. can be employed for the purification of the compound of interest.

The compound represented by the general formula (3a-1) can be produced from the compound represented by the general formula (3a-2) according to the method described in Greene's PROTECTIVE GROUPS in ORGANIC Synthesis 4th Edition, page 773 (John Wiley & Sons, Inc.). After the reaction is completed, the compound of interest is isolated from the post-reaction mixture by the usual method. As needed, recrystallization, column chromatography, etc. can be employed for the purification of the compound of interest.

The compound represented by the general formula (3a) can be produced from the compound represented by the general formula (3a-1) according to the method described in ORGANIC FUNCTION GROUP PREPARATIONS I 2nd Edition, Chapter 16, Sandler Karo (ACADEMIC PRESS, INC. (LONDON) LTD.). After the react ion is completed, the compound of interest is isolated from the post-reaction mixture by the usual method. As needed, recrystallization, column chromatography, etc. can be employed for the purification of the compound of interest.

Production Method of Intermediate (3b)

The compound represented by the general formula (3b-2) can be produced from a commercially available alkylenedioxy bromobenzene optionally halogenated at the 3- and 4-positions (3b-3) according to the method described in ORGANIC FUNCTION GROUP PREPARATIONS I 2nd Edition, Chapter 16, Sandler Karo (ACADEMIC PRESS, INC. (LONDON) LTD.). After the reaction is completed, the compound of interest is isolated from the post-reaction mixture by the usual method. As needed, recrystallization, column chromatography, etc. can be employed for the purification of the compound of interest.

The compound represented by the general formula (3b-1) can be produced by reacting the compound represented by the general formula (3b-2) with methylamine in the presence of cuprous oxide and an inert solvent.

The inert solvent used in this reaction may be any solvent that does not markedly inhibit the reaction, and examples include polar solvents such as N,N-dimethylformamide, N,N-dimethylacetamide, and 1,3-dimethyl-2-imidazolidinone. One of these inert solvents may be used alone, and also two or more of them may be used as a mixture. After the reaction is completed, the compound of interest is isolated from the post-reaction mixture by the usual method. As needed, recrystallization, column chromatography, etc. can be employed for the purification of the compound of interest.

The compound represented by the general formula (3b) can be produced from the compound represented by the general formula (3b-1) according to the method described in ORGANIC FUNCTION GROUP PREPARATIONS I 2nd Edition, Chapter 16, Sandler Karo (ACADEMIC PRESS, INC. (LONDON) LTD.). After the reaction is completed, the compound of interest is isolated from the post-reaction mixture by the usual method. As needed, recrystallization, column chromatography, etc. can be employed for the purification of the compound of interest.

Specific examples of the compound of the present invention are shown below. In the present disclosure including the following tables etc., Et stands for an ethyl group Me stands for a methyl group, MOM stands for a methoxymethyl group, and CN stands for a cyano group. Shown in the column of "Physical property value" is a melting point (° C.) or "NMR". NMR data are shown in Table 2.

[Chem. 5]

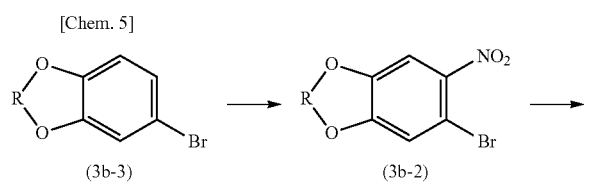

[Chem. 6]

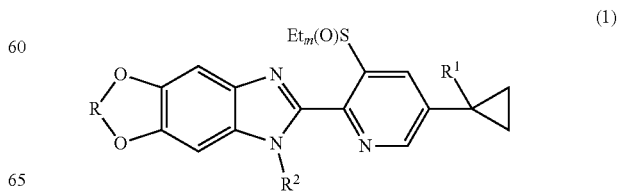

TABLE 1

| Compound No. | R¹ | R² | R | m | Physical property value |
|---|---|---|---|---|---|
| 1-1 | H | Me | CF$_2$ | 0 | 130-131 |
| 1-2 | H | Me | CF$_2$ | 1 | |
| 1-3 | H | Me | CF$_2$ | 2 | 159-160 |
| 1-4 | CN | Me | CF$_2$ | 0 | 119-120 |
| 1-5 | CN | Me | CF$_2$ | 1 | 188-189 |
| 1-6 | CN | Me | CF$_2$ | 2 | 173-175 |
| 1-7 | H | CHF$_2$ | CF$_2$ | 0 | 116-118 |
| 1-8 | H | CHF$_2$ | CF$_2$ | 1 | 203-205 |
| 1-9 | H | CHF$_2$ | CF$_2$ | 2 | 170-172 |
| 1-10 | H | Et | CF$_2$ | 0 | 105-106 |
| 1-11 | H | Et | CF$_2$ | 1 | 195-197 |
| 1-12 | H | Et | CF$_2$ | 2 | 175-177 |
| 1-13 | H | MOM | CF$_2$ | 0 | NMR |
| 1-14 | H | MOM | CF$_2$ | 1 | 123-125 |
| 1-15 | H | MOM | CF$_2$ | 2 | 187-189 |

TABLE 2

| Compound No. | ¹H-NMR Data (CDCl$_3$) |
|---|---|
| 1-13 | 8.22(d, 1H), 7.52(s, 1H), 7.34(d, 1H), 7.28(s, 1H), 5.70(s, 2H), 3.16(s, 3H), 2.90(dd, 2H), 2.01-1.94(m, 1H), 1.30(t, 3H), 1.17-1.11(m, 2H), 0.86-0.82(m, 2H) |

The agricultural and horticultural insecticide comprising the benzimidazole compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina sp., Carposina niponensis, Conogethespuncti-feralis, Synanthedon sp., Lyonetia clerkella, Papilio helenus, Colias erate poliographus, Phalera flavescens*, the species of the family Pieridae such as *Pieris brassicae* and *Pieris rapae crucivora, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*;

the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Caverius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cinc-* ticeps, *Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psyllapyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca* spp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipienspallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella;* the species of the order Hymenoptera such as *Pristomyrmex pungens, Bethylid wasps, Monomorium pharaonis, Pheidole noda, Athalia rosae, Dryocosmus kuriphilus, Formica fusca japonica, Vespid wasps, Athalia infumata infumata, Arge pagana, Athalia japonica, Acromyrmex* spp., *Solenopsis* spp., *Arge mali* and *Ochetellus glaber;* the species of the order Orthoptera such as *Homorocoryphus lineosus, Gryllotalpasp., Oxya hylaintricata, Oxyayezoensis, Locusta migratoria, Oxya japonica, Homorocoryphus jezoensis* and *Teleogryllus emma;* the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora* and *Liothrips vaneeckei;* the species of the order Acari such as Leptotrombidium akamushi, *Tetranychus ludeni, Dermacentor variabilis, Tetranychus truncatus, Ornithonyssus bacoti, Demodex canis, Tetranychus viennensis, Tetranychus kanzawai,* the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphyla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes*

*domesticus, Odontotermes formosanus, Glyptotermes nakajimai, Pericapritermes nitobei* and *Reticulitermes speratus;*
the species of the order Blattodea such as *Periplaneta fuliginosa, Blattella germanica, Blatta orientalis, Periplaneta brunnea, Blattella lituricollis, Periplaneta japonica* and *Periplaneta americana;*
the species of the order Siphonaptera such as *Pulex irritans, Ctenocephalides felis* and *Ceratophyllus gallinae;*
the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans*; and
the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, animal-parasitic mites and ticks which live in the interior of or on the exterior of animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni*, Leptotrombidium *akamushi*, Leptotrombidium *pallidum*, Leptotrombidium *fuji*, Leptotrombidium *tosa*, *Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis.*

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus.*

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. Also included are endoparasites, for example, nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

Specific Examples of the endoparasite include the following endoparasites:
from the order Enoplida, for example, *Trichuris* spp. (whipworms), *Capillaria* spp. (hairworms), *Trichomosoides* spp., *Trichinella* spp. (roundworms), etc.;
from the order Rhabditida, for example, *Micronema* spp., *Strongyloides* spp., etc.;
from the order Strongylida, for example, *Strongylus* spp. (strongyles), *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp. (nodule worms), *Chabertia* spp., *Stephanurus* spp. (*Stephanurus dentatus*), *Ancylostoma* spp. (*Ancylostoma duodenale*), *Uncinaria* spp., *Bunostomum* spp., *Globocephalus* spp., *Syngamus* spp., *Cyathostoma* spp., *Metastrongylus* spp. (lungworms), *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp. (*Angiostrongylus cantonensis*), *Aelurostrongylus* spp., *Filaroides* spp., *Parafilaroides* spp., *Trichostrongylus* spp. (*trichostrongyles*), *Haemonchus* spp. (*Haemonchus contortus*), *Ostertagia* spp., *Marshallagia* spp., *Cooperia* spp., *Nematodirus* spp. (*nematodes*), *Hyostrongylus* spp., *Obeliscoides* spp., *Amidostomum* spp., *Ollulanus* spp., etc.;
from the order Oxyurida, for example, *Oxyuris* spp. (*Oxyuris equi*), *Enterobius* spp. (pinworms), *Passalurus* spp., *Syphacia* spp., *Aspiculuris* spp., *Heterakis* spp., etc.;
from the order Ascaridia, for example, *Ascaris* spp. (ascarids), *Toxascaris* spp., *Toxocara* spp. (*Toxocara canis*), *Parascaris* spp. (*Parascaris equorum*), *Anisakis* spp., Ascaridia spp., etc.; from the order Spirurida, for example, *Gnathostoma* spp., *Physaloptera* spp., *Thelazia* spp., *Gongylonema* spp., *Habronema* spp., *Parabronema* spp., *Draschia* spp., *Dracunculus* spp. (*Dracunculus medinensis*), etc.;
from the order Filariida, for example, *Stephanofilaria* spp., *Parafilaria* spp., *Setaria* spp., *Loa* spp., *Dirofilaria* spp. (*Dirofilaria immitis*), *Litomosoides* spp., *Brugia* spp., *Wuchereria* spp., *Onchocerca* spp., etc.; and
from the order Gigantorhynchida, for example, *Filicollis* spp., *Moniliformis* spp., *Macracanthorhynchus* spp., *Prosthenorchis* spp., etc.

The ectoparasite or endoparasite control agent comprising the benzimidazole compound represented by the general formula (1) of the present invention or a salt thereof as an active ingredient is effective against not only parasites that live in the body of an intermediate or final host, but also parasites that live in the body of a reservoir host. The compound represented by the general formula (1) of the present invention is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae and adults. The compound of the present invention is capable of not only combating parasites in the living body, but also even preventing endoparasitic or ectoparasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

The use in mammals and birds will be described below. For the control of ectoparasites or endoparasite in mammals and birds using the compound of the present invention, an effective amount of the compound of the present invention with pharmaceutical excipients can be delivered by oral administration; parenteral administration such as injection (intramuscular, subcutaneous, intravenous, intraperitoneal); transdermal administration such as dipping, spraying, bathing, washing, pouring-on, spotting-on, or dusting; or transnasal administration. For the administration of the compound of the present invention, molded products containing the compound, such as strips, plates, bands, collars, earmarks, limb bands, and label devices, can also be used. The compound of the present invention can be formulated into any dosage form suitable for the administration route selected in administration.

Examples of the dosage form of the compound of the present invention include solid preparations, such as powders, granules, wettable powders, pellets, tablets, bolus, capsules, and molded products containing the compound of the present invention; water-miscible or oily liquid preparations, such as injectable solutions, oral solutions, solutions for use on the animal skin or in body cavities (spot-on solutions, pour-on solutions), and emulsions; suspension preparations such as flowables; and semi-solid preparations such as ointments and gels. The solid preparations can be used mainly for oral administration or for transdermal administration after dilution with water, or for environmental treatment.

The solid preparations can be produced by mixing the compound of the present invention, and if necessary an adjuvant, with an appropriate filler and then shaping the mixture into a desired form. Examples of the appropriate filler include inorganic substances such as carbonate salts, hydrogen carbonate salts, phosphate salts, aluminum oxide, silica, and clay; and organic substances such as sugar, cellulose, ground cereals, and starch.

The injectable solutions can be administered intravenously, intramuscularly, or subcutaneously. The injectable solutions can be produced by dissolving the compound of the present invention in an appropriate solvent, and if necessary, adding excipients such as solubilizing agents, acids, bases, buffer salts, antioxidants, and protecting agents to the solution. Examples of the appropriate solvent include water, ethanol, butanol, benzyl alcohol, glycerin, propylene glycol, polyethylene glycol, N-methyl pyrrolidone, and a mixture thereof, physiologically acceptable vegetable oils, and synthetic oils suitable for injection. Examples of the solubilizing agent include polyvinyl pyrrolidone, polyoxyethylated castor oil, and polyoxyethylated sorbitan ester. Examples of the protecting agent include benzyl alcohol, trichlorobutanol, p-hydroxybenzoic acid ester, and n-butanol.

The oral solutions can be administered directly or after dilution. The oral solutions can be prepared according to well-established and conventional pharmaceutical technology as with the injectable solutions.

The flowables, emulsions, and the like can be transdermally administered directly or after dilution, or administered in an environment-friendly manner.

The solutions for use on the animal skin can be administered by pouring on, spreading, rubbing in, spraying, dispersing or dipping (dipping, bathing, or washing) or applying. These solutions can be prepared as described above for the injectable solutions.

The pour-on solutions and spot-on solutions are dripped or sprayed onto a defined area of the animal skin, and thereby the compound of the present invention is allowed to permeate through the animal skin and act systemically. The pour-on solutions and spot-on solutions can be prepared by dissolving, suspending, or emulsifying the active ingredient in an appropriate solvent or mixed solvent suitable for use on the animal skin. If necessary, an adjuvant such as a surfactant, a colorant, an absorption enhancer, an antioxidant, a defoamer, a light stabilizer, and/or an adhesive may be contained. Examples of the solvent include water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methyl pyrrolidone, and 2,2-dimethyl-4-oxy-methylene-1,3-dioxolane. Examples of the absorption enhancer include DMSO, isopropyl myristate, dipropylene glycol pelargonate, silicone oil, aliphatic ester, triglyceride, and fatty alcohol. Examples of the antioxidant include sulfite salts, metabisulfite salts, ascorbic acid, butylated hydroxytoluene, butylated hydroxyanisole, and tocopherol.

The emulsions can be delivered by oral administration, transdermal administration, or injection. The emulsions can be prepared by dissolving the active ingredient in a hydrophobic or hydrophilic phase and homogenizing the solution with the other phase solvent with the addition of an appropriate emulsifier and if necessary an adjuvant such as a colorant, an absorption enhancer, a protecting agent, an antioxidant, a light-shielding agent, and/or a thickener.

Examples of the hydrophobic phase (oil) include paraffin oil, silicone oil, sesame oil, almond oil, castor oil; synthetic triglycerides, medium-chain fatty acid triglycerides (triglycerides with caprylic acid ($C_8$) or capric acid ($C_{10}$), etc.); esters such as ethyl stearate, di-n-butyryl adipate, hexyl laurate, dipropylene glycol pelargonate, esters of branched short-chain fatty acids and saturated fatty acids of $C_{16}$-$C_{18}$ chain length, isopropyl myristate, isopropyl palmitate, caprylic or capric acid esters of saturated fatty alcohols of $C_{12}$-$C_{18}$ chain length, isopropyl stearate, oleyl oleate, decyl oleate, ethyl oleate, ethyl lactate, waxy fatty acid ester, dibutyl phthalate, and diisopropyl adipate; and alcohols such as isotridecyl alcohol, 2-octyldodecanol, cetyl stearyl alcohol, and oleyl alcohol.

Examples of the hydrophilic phase include water, propylene glycol, glycerin, and sorbitol.

Examples of the emulsifier include nonionic surfactants such as polyoxyethylated castor oil, polyoxyethylated sorbitan monoolefinate, sorbitan monostearate, glyceryl monostearate, polyoxyethyl stearate, and alkylphenol polyglycol ether; amphoteric surfactants such as disodium N-lauryl β-iminodipropionate and lecithin; anionic surfactants such as sodium lauryl sulfate, fatty alcohol ether sulfate, and monoethanolamine salts of mono-/di-alkyl polyglycol orthophosphoric acid ester; and cationic surfactants such as cetyltrimethylammonium chloride.

Examples of the defoamer include Shin-etsu silicone (manufactured by Shin-Etsu Chemical Co., Ltd.), silicone SM 5512 (manufactured by Toray Dow Corning Silicone Co. Ltd.), ANTIFOAM E-20 (manufactured by Kao Corporation), and SILFOAM SE 39 (manufactured by Wacker Asahikasei Silicone Co., Ltd.).

Other adjuvants include carboxymethyl cellulose, methyl cellulose, polyacrylate, alginate, gelatin, gum arabic, polyvinyl pyrrolidone, polyvinyl alcohol, methyl vinyl ether, maleic anhydride copolymers, polyethylene glycol, waxes, and colloidal silica.

The semi-solid preparations can be administered by applying or spreading them on the animal skin or introducing them into body cavities. The gels can be prepared by preparing a solution as described above for the injectable solutions and adding, to the solution, a thickener in an amount sufficient to give a clear, ointment-like, viscous substance.

In the case where the ectoparasite or endoparasite control agent of the present invention is used as a pharmaceutical for animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or in divided doses.

The concentration of the active ingredient in the ectoparasite or endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that needs to be diluted to a suitable concentration before use.

The ectoparasite or endoparasite control agent of the present invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural and horticultural insecticide comprising the benzimidazole compound represented by the general formula (1) of the present invention or a salt thereof as an active ingredient will be described hereinafter. The compound of the present invention has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives, Welsh onions, etc.), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like. Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae*; *Bacillus thuringiensis* S-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: S-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP0374753A, WO93/07278, WO95/34656, EP0427529A, EP451878A, WO03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated with the agricultural and horticultural insecticide of the present invention in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared by the usual method for preparing agrochemical formulations.

That is, the benzimidazole compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal ectoparasite or endoparasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, polyoxyethylene ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl 0,0-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, yenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacyl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsine, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as Monacrosporium phymatophagum, Steinernema carpocapsae, Steinernema kushidai and Pasteuria *penetrans*; microbial pesticides used as a microbicide, such as *Trichoderma* lignorum, *Agrobacterium* radiobactor, avirulent *Erwinia carotovora* and *Bacillus subtilis*; and biopesticides used as a herbicide, such as *Xanthomonas campestris*. Such a combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

The benzimidazole compound represented by the general formula (1) of the present invention or a salt thereof is also suitable for the disinfection of parasites that live in the interior of or on the exterior of animals such as humans, domestic animals and pets. The animal may be a non-human animal.

The present invention also includes an animal ectoparasite or endoparasite control agent comprising the compound of the present invention or a salt thereof as an active ingredient; and a method for controlling animal ectoparasites or endoparasites, comprising treating animal ectoparasites or endoparasites with the animal ectoparasite or endoparasite control agent. The compound of the present invention can be used by spot-on or pour-on application usually to one site or two sites on the skin of an animal such as a cat or a dog. The application area is usually 5 to 10 cm². Once applied, the compound of the present invention preferably diffuses throughout the animal's body and then dries without crystallization or changes in visual appearance or texture. The preferable amount of the compound used is selected from the range of about 0.1 to 10 mL according to the weight of the animal, and in particular, is about 0.5 to 1 mL for a cat and about 0.3 to 3 mL for a dog.

The ectoparasite or endoparasite control agent of the present invention is effective against, for example, the following animal ectoparasites or endoparasites. Siphonaptera parasites include the species of the genus *Pulex* such as *Pulex irritans*; the species of the genus *Ctenocephalides* such as *Ctenocephalides felis* and *Ctenocephalides canis*; the species of the genus *Xenopsylla* such as *Xenopsylla cheopis*; the species of the genus *Tunga* such as *Tunga penetrans*; the species of the genus *Echidnophaga* such as *Echidnophaga gallinacea*; and the species of the genus *Nosopsyllus* such as *Nosopsyllus fasciatus*.

Siphunculata parasites include the species of the genus *Pediculus* such as *Pediculus humanus capitis*; the species of the genus *Pthirus* such as *Pthirus pubis*; the species of the genus *Haematopinus* such as *Haematopinus eurysternus* and *Haematopinus suis*; the species of the genus *Damalinia* such as *Damalinia ovis* and *Damalinia bovis*; the species of the genus *Linognathus* such as *Linognathus vituli* and *Linognathus ovillus* (parasitic on the trunk of a sheep's body); and the species of the genus *Solenopotes* such as *Solenopotes capillatus*.

Mallophaga parasites include the species of the genus *Menopon* such as *Menopon gallinae*; Trimenopon spp.; *Trinoton* spp.; the species of the genus *Trichodectes* such as *Trichodectes canis*; the species of the genus *Felicola* such as *Felicola* subrostratus; the species of the genus *Bovicola* such as *Bovicola bovis*; the species of the genus *Menacanthus* such as *Menacanthus stramineus; Werneckiella* spp.; and *Lepikentron* spp.

Hemiptera parasites include the species of the genus *Cimex* such as *Cimex lectularius* and *Cimex hemipterus*; the species of the genus *Reduvius* such as *Reduvius senilis*; the species of the genus *Arilus* such as *Arilus critatus*; the species of the genus *Rhodnius* such as *Rhodnius prolixus*; the species of the genus *Triatoma* such as *Triatoma rubrofasciata*; and *Panstrongylus* spp.

Acarina parasites include the species of the genus *Amblyomma* such as *Amblyomma americanum* and *Amblyomma maculatum*; the species of the genus *Boophilus* such as *Boophilus microplus* and *Boophilus annulatus*; the species of the genus *Dermacentor* such as *Dermacentor variabilis, Dermacentor taiwanensis* and *Dermacentor andersoni*; the species of the genus *Haemaphysalis* such as *Haemaphysalis longicornis, Haemaphysalis flava* and *Haemaphysalis campanulata*; the species of the genus *Ixodes* such as *Ixodes ovatus, Ixodes persulcatus, Ixodes scapularis, Ixodes pacificus* and *Ixodes holocyclus*; the species of the genus *Rhipicephalus* such as *Rhipicephalus sanguineus* and *Rhipicephalus appendiculatus*; the species of the genus *Argas* such as *Argas persicus*; the species of the genus *Ornithodoros* such as *Ornithodoros hermsi* and *Ornithodoros turicata*; the species of the genus *Psoroptes* such as *Psoroptes ovis* and *Psoroptes equi*; the species of the genus *Knemidocoptes* such as *Knemidocoptes mutans*; the species of the genus *Notoedres* such as *Notoedres cati* and *Notoedres muris*; the species of the genus *Sarcoptes* such as *Sarcoptes scabiei*; the species of the genus *Otodectes* such as *Otodectes cynotis*; the species of the genus *Listrophorus* such as *Listrophorus gibbus; Chorioptes* spp.; *Hypodectes* spp.; *Pterolichus* spp.; *Cytodites* spp.; *Laminosioptes* spp.; the species of the genus *Dermanyssus* such as *Dermanyssus gallinae*; the species of the genus *Ornithonyssus* such as *Ornithonyssus sylviarum* and *Ornithonyssus bacoti*; the species of the genus *Varroa* such as *Varroa jacobsoni*; the species of the genus *Cheyletiella* such as *Cheyletiella yasguri* and *Cheyletiella blakei; Ornithocheyletia* spp.; the species of the genus *Demodex* such as *Demodex canis* and *Demodex cati*; Myobia spp.; *Psorergates* spp.; and the species of the genus *Trombicula* such as *Trombicula akamushi, Trombicula pallida* and *Trombicula scutellaris*. Preferred are Siphonaptera parasites, Siphunculata parasites and Acarina parasites.

The animals to which the ectoparasite or endoparasite control agent of the present invention is administrable can be host animals for the above-mentioned animal ectoparasites or endoparasites. Such animals are usually homeotherms and poikilotherms which are bred as domestic animals or pets. Such homeotherms include mammals such as cattle, buffalos, sheep, goats, pigs, camels, deer, fallow deer, reindeer, horses, donkeys, dogs, cats, rabbits, ferrets, mice, rats, hamsters, squirrels and monkeys; fur-bearing animals such as minks, chinchillas and raccoons; and birds such as chickens, geese, turkeys, domestic ducks, pigeons, parrots and quails. The above-mentioned poikilotherms include reptiles such as tortoises, sea turtles, pond sliders, Japanese pond turtles, lizards, iguanas, chameleons, geckos, pythons, colubrid snakes and cobras. Preferred are homeotherms, and more preferred are mammals such as dogs, cats, cattle, horses, pigs, sheep and goats.

Since the control agent of the present invention is unlikely to damage or impact natural predators and useful insects (hereinafter also referred to as nontarget organisms), two or more insect pest control methods etc. can be rationally combined for use.

Examples of the nontarget organism include natural predators such as *Phytoseiulus persimilis, Neoseiulus californicus, Amblyseius swirskii* Athias-Henriot, *Neoseiulus womersleyi*, and *Typhlodromus vulgaris*; and useful insects such as honey bees, western honey bees (*Apis mellifera*), bumblebees, buff-tailed bumblebees (*Bombus terrestris*), horned-face bees (Osmia cornifrons), and domestic silkmoths (*Bombyx mori*).

Hereinafter, the production examples of representative compounds of the present invention and their intermediates will be described in more detail, but the present invention is not limited only to these examples.

EXAMPLES

Reference Example 1

Production Method of N-(2,2-diflorobenzo[d][1,3]dioxol-5-yl)acetamide

[Chem. 7]

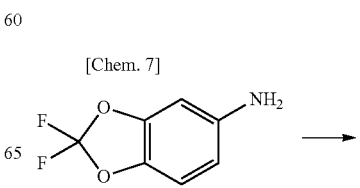

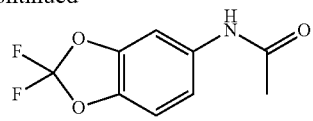

5-Amino-2,2-diflorobenzo[d][1,3]dioxole (980 mg, 5.66 mmol) was dissolved in pyridine (10 mL), and acetic anhydride (1.2 Eq, 544 mg) was added. The mixture was allowed to react at room temperature for 2 hours. The reaction mixture was concentrated, and after toluene was added, the mixture was concentrated again. This procedure was repeated twice for pyridine removal, and the residue was used for the next reaction.

Reference Example 2

Production Method of
N-(2,2-difluoro-6-nitrobenzo[d][1,3]dioxol-5-yl)acetamide

[Chem. 8]

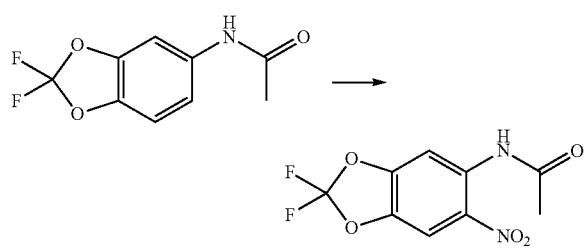

Acetic acid (15 mL) was added to the residue obtained at the previous step, and white fuming nitric acid (441 mg, 1.2 Eq) was added slowly. The mixture was allowed to react at room temperature for 1 hour and then at 60° C. for 1 hour. At the same temperature, white fuming nitric acid (450 mg, 1.2 Eq) was added, and the mixture was allowed to react for 3 hours. This procedure was repeated. After the disappearance of the starting material was confirmed by TLC, the reaction mixture was added to iced water, and the water-containing mixture was extracted with ethyl acetate 3 times. The combined organic layer was dried over sodium sulfate and concentrated to give the desired compound (1.17 g).

Reference Example 3

Production Method of
2,2-difluorobenzo[d][1,3]dioxole-5,6-diamine (intermediate)

[Chem. 9]

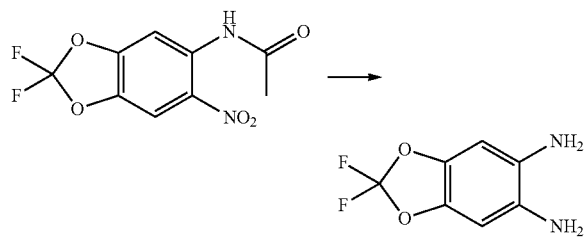

The nitro compound (1.17 g, 4.5 mmol) obtained at the previous step was dissolved in methanol (30 mL), and 28% sodium methoxide (4.3 g, 5 Eq) was added under ice cooling. The mixture was allowed to react for 1 hour. Acetic acid (50 mL) was added to the reaction mixture, and the mixture was allowed to react for 10 minutes. Water was added to the reaction mixture, and extraction with ethyl acetate was performed 3 times. The combined organic layer was dried over sodium sulfate and concentrated. The residue was dissolved in ethanol (50 mL) and transferred to a medium-pressure reaction vessel. 5% Pd—C(wet, 200 mg) was added, and the mixture was allowed to react under a hydrogen atmosphere (3 atm) for 2 hours. The catalyst was removed from the reaction mixture, and the filtrate was concentrated. A saturated aqueous sodium bicarbonate solution was added to the residue, and extraction with ethyl acetate was performed 3 times. The combined organic layer was dried over sodium sulfate and concentrated to give the desired compound (780 mg).

Reference Example 4

Production Method of
6-(5-cyclopropyl-3-ethylthiopyridin-2-yl)-2,2-difluoro-5H-[1,3]dioxolo[4',5':4,5]benzo[1,2-d]imidazole

[Chem. 10]

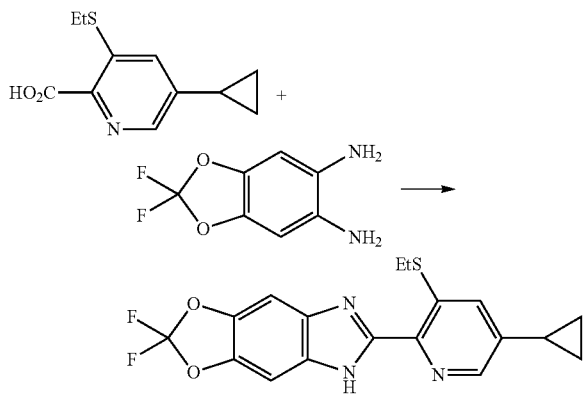

The diamine obtained at the previous step and 5-cyclopropyl-3-ethylthiopicolinic acid (925 mg, 1 Eq) were dissolved in THF (10 mL) and triethylamine (5 mL), and 1-methyl-2-chloropyridinium iodide (1.2 g, 1.1 Eq) was added. The mixture was allowed to react at room temperature for 30 minutes and then at 50° C. for 1 hour. Water was added to the reaction mixture, and extraction with ethyl acetate was performed 3 times. The combined organic layer was dried over sodium sulfate and concentrated. P-toluenesulfonic acid (2.2 g, 3 Eq) and N-methyl pyrrolidone (10 mL) were added to the residue, and the mixture was stirred at 150° C. for 2 hours. The reaction mixture was allowed to cool down to room temperature, and the residue was subjected to column chromatography to give the desired compound (857 mg, 40%, 6 steps).

Reference Example 5

Production Method of
5-bromo-2,2-difluoro-6-nitrobenzo[d][1,3]dioxole

[Chem. 11]

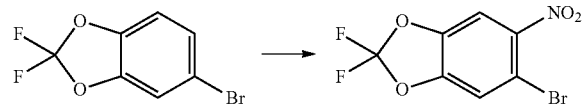

5-Bromo-2,2-diflorobenzo[d][1,3]dioxole (6 g, 25 mmol) was dissolved in concentrated sulfuric acid (25 mL), and 63% nitric acid (1.5 Eq, 3.5 g) was added. The mixture was stirred at room temperature for 30 minutes. After the disappearance of the starting material was confirmed by TLC, the reaction mixture was added to iced water, and the water-containing mixture was extracted with ethyl acetate 3 times. The combined organic layer was dried over sodium sulfate and concentrated. The residue was subjected to column chromatography to give the desired compound (7.7 g, 99%).

Reference Example 6

Production Method of
2,2-difluoro-N-methyl-6-nitrobenzo[d][1,3]dioxole-5-amine

[Chem. 12]

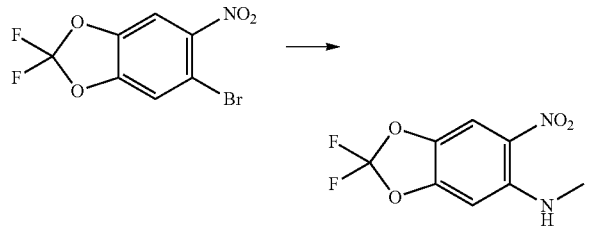

The nitro compound (5.62 g, 20 mmol) produced at the previous step was dissolved in DMF (20 mL), and cuprous oxide (1.43 g, 0.5 Eq) was added. A 40% solution of methylamine (3.88 g, 2.5 Eq) in methanol was added dropwise under ice cooling, and the mixture was stirred at room temperature for 4 hours. A saturated aqueous ammonium chloride solution and sodium chloride were added to the reaction mixture, and extraction with ethyl acetate was performed 4 times. The combined organic layer was dried over sodium sulfate, and the residue was subjected to column chromatography to give the desired compound (2.26 g, 49%).

Reference Example 7

Production Method of
2,2-difluoro-$N^5$-methylbenzo[d][1,3]dioxole-5,6-diamine

[Chem. 13]

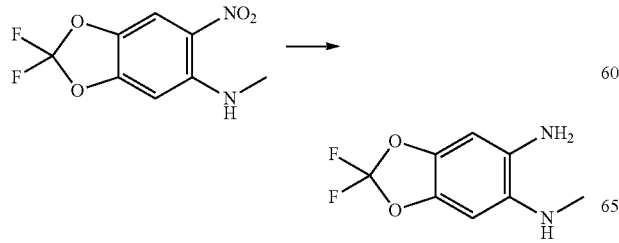

The methylamino compound (2.26 g, 9.74 mmol) obtained at the previous step was transferred to a medium-pressure reaction vessel, and 5% Pd—C(wet, 200 mg) was added. The mixture was stirred under a hydrogen atmosphere (3 atm) for 2 hours. The reaction mixture was filtered through Celite for removal of the catalyst, and the filtrate was concentrated. A saturated aqueous sodium bicarbonate solution was added to the residue, and extraction with ethyl acetate was performed 3 times. The combined organic layer was dried over sodium sulfate and concentrated to give the desired compound (1.83 g).

Production Example 1

Production Method of
6-(5-cyclopropyl-3-ethylthiopyridin-2-yl)-2,2-difluoro-5-me thyl-5H-[1,3]dioxolo[4',5':4,5]benzo[1,2-d]imidazole (compound number 1-1)

[Chem. 14]

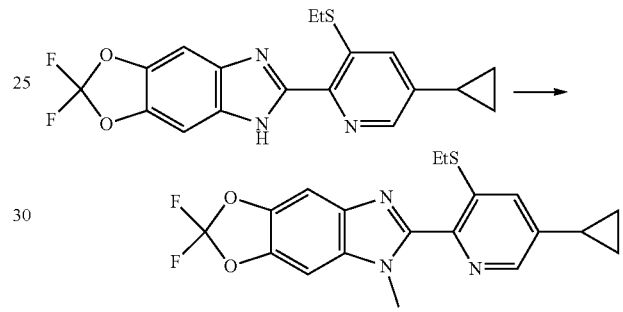

The benzo[1,2-d]imidazole compound (309 mg, 0.824 mmol) obtained in Reference Example 4 and cesium carbonate (534 mg, 2 Eq) were dissolved in DMF (2 mL), and methyl iodide (177 mg, 1.5 Eq) was added. The mixture was stirred at room temperature for 3 hours, then diluted with acetone, and concentrated. The residue was subjected to column chromatography to give the desired compound (246 mg, 77%).

Production Example 2

Production Method of
6-(5-cyclopropyl-3-ethylsulfonyl-pyridin-2-yl)-2,2-difluoro-5-methyl-5H-[1,3]dioxolo[4',5':4,5]benzo[1,2-d]imidazole (Compound Number 1-3)

[Chem. 15]

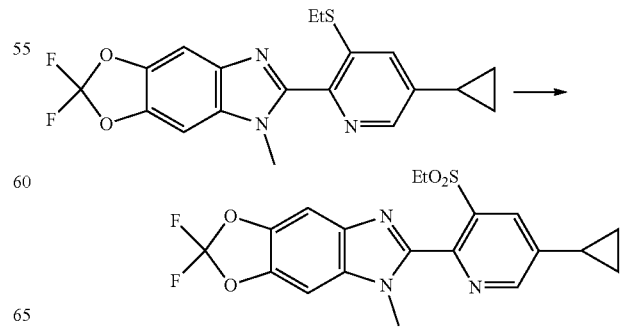

The methyl compound (217.4 mg, 0.559 mmol) obtained in Production Example 1 was dissolved in ethyl acetate (5 mL), and m-chloroperoxybenzoic acid (238 mg, 1.6 Eq) was added. The mixture was stirred for 3 hours. DMSO (1 mL) was added, and the mixture was concentrated. The residue was subjected to column chromatography to give the desired compound (142 mg, 60%).

Production Example 3

Production Method of 6-(5-cyclopropyl-3-ethylthiopyridin-2-yl)-2,2-difluoro-5-difluoromethyl-5H-[1,3]dioxolo[4',5':4,5]benzo[1,2-d]imidazole (compound number 1-7)

[Chem. 16]

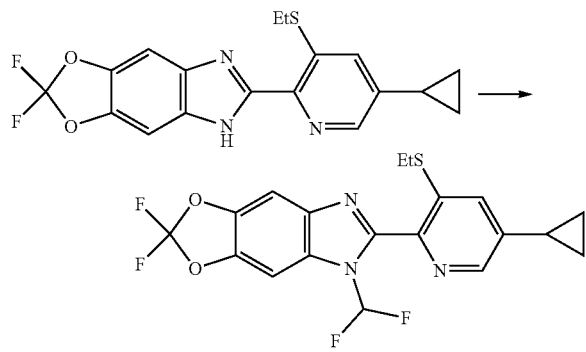

The benzo[1,2-d]imidazole compound (191 mg, 0.509 mmol) obtained in Reference Example 4 was dissolved in DMF (3 mL), and sodium hydride (41 mg, 2 Eq) was added. The mixture was stirred at room temperature for 30 minutes, and with slow bubbling of chlorodifluoromethane gas, stirred at room temperature for 2 hours. The residue was subjected to column chromatography to give the desired compound (138 mg, 64%).

Production Example 4

Production Method of 
6-(5-cyclopropyl-3-ethylsulfonylpyridin-2-yl)-2,2-difluoro-5-difluoromethyl-5H-[1,3]dioxolo[4',5':4,5]benzo[1,2-d]imid azole (compound number 1-9) and
6-(5-cyclopropyl-3-ethylsulfinylpyridin-2-yl)-2,2-difluoro-5-difluoromethyl-5H-[1,3]dioxolo[4',5':4,5]benzo[1,2-d]imid azole (compound number 1-8)

[Chem. 17]

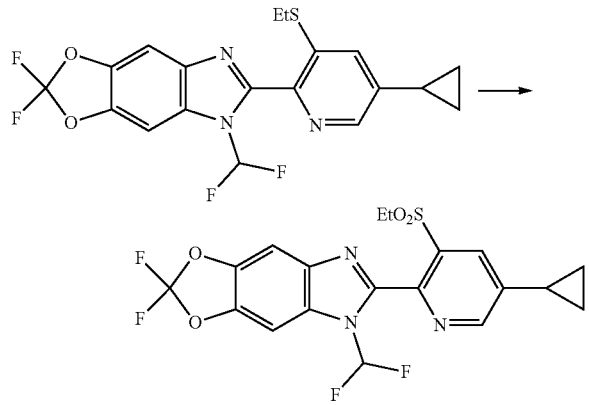

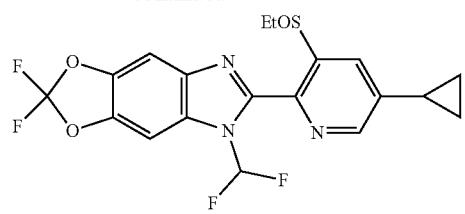

The difluoromethyl compound (117 mg, 0.276 mmol) obtained at the previous step was dissolved in ethyl acetate (5 mL), and m-chloroperoxybenzoic acid (95 mg, 1.3 Eq) was added. The mixture was stirred for 2 hours. Triethylamine (1 mL) was added, and the mixture was diluted with acetone. Silica gel was added, and the mixture was concentrated. The residue was subjected to column chromatography to give a sulfonyl compound (77 mg, 61%) and a sulfinyl compound (30 mg, 25%).

Hereinafter, examples of formulations containing the compound of the present invention are shown, but the present invention is not limited thereto. In the formulation examples, "part(s)" means part(s) by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate (weight ratio of 1:1) | 10 parts |

The above ingredients were uniformly mixed for dissolution to give an emulsifiable concentrate formulation.

Formulation Example 2

| | |
|---|---|
| Compound of the present invention | 3 parts |
| Clay powder | 82 parts |
| Diatomite powder | 15 parts |

The above ingredients were uniformly mixed and then pulverized to give a dust formulation.

Formulation Example 3

| | |
|---|---|
| Compound of the present invention | 5 parts |
| Mixture of bentonite powder and clay powder | 90 parts |
| Calcium lignosulfonate | 5 parts |

The above ingredients were uniformly mixed. After addition of an appropriate volume of water, the mixture is kneaded, granulated and dried to give a granular formulation.

Formulation Example 4

| | |
|---|---|
| Compound of the present invention | 20 parts |
| Kaolin and synthetic high-dispersion silicic acid | 75 parts |
| Mixture of polyoxyethylene nonylphenyl ether and calcium alkylbenzene sulfonate (weight ratio of 1:1) | 5 parts |

The above ingredients were uniformly mixed and then pulverized to give a wettable powder formulation.

Formulation Example 5

| | |
|---|---|
| Compound of the present invention | 20 parts |
| Polyoxyethylene lauryl ether | 3 parts |
| Sodium dioctyl sulfosuccinate | 3.5 parts |
| Dimethyl sulfoxide | 37 parts |
| 2-Propanol | 36.5 parts |

The above ingredients were uniformly mixed for dissolution to give a water-miscible liquid preparation.

Formulation Example 6

| | |
|---|---|
| Compound of the present invention | 2 parts |
| Dimethyl sulfoxide | 10 parts |
| 2-Propanol | 35 parts |
| Acetone | 53 parts |

The above ingredients were uniformly mixed for dissolution to give a solution for spraying.

Formulation Example 7

| | |
|---|---|
| Compound of the present invention | 5 parts |
| Hexylene glycol | 50 parts |
| Isopropanol | 45 parts |

The above ingredients were uniformly mixed for dissolution to give a solution for transdermal administration.

Formulation Example 8

| | |
|---|---|
| Compound of the present invention | 5 parts |
| Propylene glycol monomethyl ether | 50 parts |
| Dipropylene glycol | 45 parts |

The above ingredients were uniformly mixed for dissolution to give a solution for transdermal administration.

Formulation Example 9

| | |
|---|---|
| Compound of the present invention | 2 parts |
| Light liquid paraffin | 98 parts |

The above ingredients were uniformly mixed for dissolution to give a solution for transdermal (pour-on) administration.

Formulation Example 10

| | |
|---|---|
| Compound of the present invention | 2 parts |
| Light liquid paraffin | 58 parts |
| Olive oil | 30 parts |
| Medium-chain fatty acid triglyceride (ODO-H: manufactured by Nisshin OilliO Group, Ltd.) | 9 parts |
| Silicone-based defoamer (trade name: Shin-etsu silicone, manufactured by Shin-Etsu Chemical Co., Ltd.) | 1 part |

The above ingredients were uniformly mixed for dissolution to give a solution for transdermal (pour-on) administration.

Hereinafter, test examples in connection with the present invention are shown, but the present invention is not limited thereto.

Test Example 1

Test for Control Efficacy on *Myzus persicae*

Chinese cabbage plants were planted in plastic pots (diameter: 8 cm, height: 8 cm), Green peach aphids (*M. persicae*) were propagated on the plants, and the number of surviving Green peach aphids in each pot was counted. The benzimidazole compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate}=100-\{(T \times Ca)/(Ta \times C)\} \times 100 \qquad [\text{Math. 1}]$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-1, 1-3, 1-4, 1-5, 1-6, 1-11, 1-12, 1-13, and 1-15 of the present invention showed the activity level evaluated as A.

Test Example 2

Insecticidal test on *Laodelphax striatellus* The benzimidazole compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of L. striatellus, and then the glass test tubes were capped with cotton plugs. At 8 days after the inoculation, the numbers of surviving larvae and dead larvae of L. striatellus were counted, the corrected mortality rate was calculated according to the formula shown below, and the insecticidal efficacy was evaluated according to the criteria shown below.

Corrected mortality rate (%)=100×(Survival rate in a non-treatment plot−Survival rate in a treatment plot)/Survival rate in a non-treatment plot     [Math. 2]

Corrected Mortality Rate

A: the corrected mortality rate is 100%.

B: the corrected mortality rate is 90 to 99%.

C: the corrected mortality rate is 80 to 89%.

D: the corrected mortality rate is 50 to 79%.

As a result, the compounds 1-1, 1-3, 1-5, 1-6, 1-11, 1-12, 1-13, 1-14, and 1-15 showed the activity level evaluated as A in terms of the corrected mortality rate of L. striatellus.

Test Example 3

Insecticidal test on Plutella xylostella

Adults of P. xylostella were released onto Chinese cabbage seedlings and allowed to lay eggs thereon. At 2 days after the release of the adults, the Chinese cabbage seedlings with laid eggs were dipped for about 30 seconds in agrochemical formulations diluted to 500 ppm, each of which contained a different benzimidazole compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate of P. xylostella was calculated according to the formula shown below, and the insecticidal efficacy was evaluated according to the criteria of Test Example 2. This test was conducted in triplicate using 10 adults of P. xylostella per plot.

Corrected mortality rate (%)=100×(Number of hatched larvae in a non-treatment plot−Number of hatched larvae in a treatment plot)/Number of hatched larvae in a non-treatment plot     [Math. 3]

As a result, the compounds 1-1, 1-3, 1-4, 1-5, 1-6, 1-7, 1-9, 1-10, 1-11, 1-12, 1-13, 1-14, and 1-15 showed the activity level evaluated as A in terms of the corrected mortality rate of P. xylostella.

Test Example 4

Larval motility assay on Haemonchus contortus DMSO diluted solutions of various compounds of the present invention were added at the final concentration of 50 ppm to the wells of a 96-well plate containing a predetermined conditioned medium. Twenty L1 stage larvae of H. contortus were introduced into each well of the 96-well plate. The plate was allowed to stand for 4 days, and then larval motility was examined. The percent motility inhibition in the wells of each treatment was calculated relative to the wells of treatment with DMSO only.

As a result, the compound 1-3 of the present invention showed a percent motility inhibition of 50% or more.

Test Example 5

Larval Motility Assay on Dirofilaria immitis

Five hundred L1 stage larvae of D. immitis were diluted in a predetermined conditioned medium and introduced into each well of a 96-well plate. DMSO diluted solutions of various compounds of the present invention were added at the final concentration of 50 ppm to the wells of the 96-well plate. The plate was allowed to stand for 3 days, and then larval motility was examined. The percent motility inhibition in the wells of each treatment was calculated relative to the wells of treatment with DMSO only.

As a result, the compounds 1-3 and 1-6 of the present invention showed inhibitory efficacy against larvae of D. immitis with a percent motility inhibition of 50% or more.

Test Example 6

Assay for Oral Parasiticidal Activity Against Adults of Ctenocephalides felis

Newly-emerged adults of C. felis were placed into test cages (10 adults per test cage). DMSO diluted solutions of various compounds of the present invention were added to aliquots of bovine blood at the final concentration of 50 ppm and orally administered to the adults of C. felis using a feeder. The mortality rate was examined on the following day. Aberrant adults were regarded as the dead.

As a result, the compounds 1-3 and 1-6 of the present invention showed parasiticidal activity against adults of C. felis with a mortality rate of 50% or more.

Test Example 7

Assay for Transdermal Parasiticidal Activity Against Nymphs of Rhipicephalus sanguineus DMSO diluted solutions of various compounds of the present invention were individually diluted to the final concentration of 100 ppm with an acetone/triton solution and applied to the inside of vented sample bottles. After overnight drying, ten nymphs of R. sanguineus were introduced into each bottle, and the mortality rate was examined two days later. Aberrant adults were regarded as the dead.

As a result, the compounds 1-3 and 1-6 of the present invention showed parasiticidal activity against nymphs of R. sanguineus with a mortality rate of 50% or more.

INDUSTRIAL APPLICABILITY

The compound of the present invention is highly effective for the control of a wide range of agricultural and horticultural pests and animal ectoparasites and endoparasites and thus is useful.

The invention claimed is:

1. A benzimidazole compound represented by:

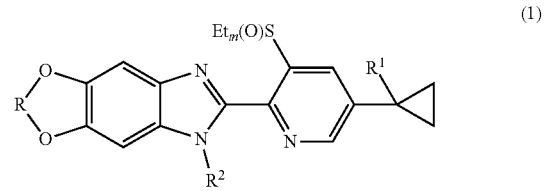

wherein $R^1$ represents (a1) a hydrogen atom; or (a2) a cyano group,

R² represents
(b1) a ($C_1$-$C_6$) alkyl group;
(b2) a ($C_1$-$C_6$) alkoxy ($C_1$-$C_6$) alkyl group; or
(b3) a halo ($C_1$-$C_6$) alkyl group,
R represents
(c1) a ($C_1$-$C_3$) alkylene group; or
(c2) a halo ($C_1$-$C_3$) alkylene group, and
m represents 0, 1, or 2, or
a salt thereof.

2. The benzimidazole compound or the salt according to claim 1, wherein
R¹ represents
(a1) a hydrogen atom; or
(a2) a cyano group,
R² represents
(b1) a ($C_1$-$C_6$) alkyl group;
(b2) a ($C_1$-$C_6$) alkoxy ($C_1$-$C_6$) alkyl group; or
(b3) a halo ($C_1$-$C_6$) alkyl group,
R represents
(c2) a halo ($C_1$-$C_3$) alkylene group, and
m represents 0, 1, or 2.

3. The benzimidazole compound or the salt according to claim 1, wherein
R¹ represents (a1) a hydrogen atom,
R² represents (b1) a ($C_1$-$C_6$) alkyl group,
R represents (c2) a halo ($C_1$-$C_3$) alkylene group, and
m represents 2.

4. An agricultural and horticultural insecticide comprising the benzimidazole compound or the salt according to claim 1 as an active ingredient.

5. A method for using an agricultural and horticultural insecticide, the method comprising treating plants or soil with an effective amount of the benzimidazole compound or the salt according to claim 1.

6. An animal ectoparasite or endoparasite control agent comprising an effective amount of the benzimidazole compound or the salt according to claim 1 as an active ingredient.

7. A method for using an animal ectoparasite or endoparasite control agent, the method comprising transdermally applying or orally administering an effective amount of the benzimidazole compound or the salt according to claim 1 to an animal.

8. An agricultural and horticultural insecticide comprising the benzimidazole compound or the salt according to claim 2 as an active ingredient.

9. An agricultural and horticultural insecticide comprising the benzimidazole compound or the salt according to claim 3 as an active ingredient.

10. A method for using an agricultural and horticultural insecticide, the method comprising treating plants or soil with an effective amount of the benzimidazole compound or the salt according to claim 2.

11. A method for using an agricultural and horticultural insecticide, the method comprising treating plants or soil with an effective amount of the benzimidazole compound or the salt according to claim 3.

12. An animal ectoparasite or endoparasite control agent comprising an effective amount of the benzimidazole compound or the salt according to claim 2 as an active ingredient.

13. An animal ectoparasite or endoparasite control agent comprising an effective amount of the benzimidazole compound or the salt according to claim 3 as an active ingredient.

14. A method for using an animal ectoparasite or endoparasite control agent, the method comprising transdermally applying or orally administering an effective amount of the benzimidazole compound or the salt according to claim 2 to an animal.

15. A method for using an animal ectoparasite or endoparasite control agent, the method comprising transdermally applying or orally administering an effective amount of the benzimidazole compound or the salt according to claim 3 to an animal.

* * * * *